United States Patent [19]
Fujii et al.

[11] 3,975,424
[45] Aug. 17, 1976

[54] METHOD FOR MANUFACTURE OF TETRAFLUOROTEREPHTHALONITRILE

[75] Inventors: Shozo Fujii; Kan Inukai, both of Nagoya, Japan

[73] Assignee: Agency of Industrial Science & Technology, Tokyo, Japan

[22] Filed: July 7, 1975

[21] Appl. No.: 593,544

[30] Foreign Application Priority Data
July 4, 1974  Japan.............................. 49-76714

[52] U.S. Cl. ............................................ 260/465 G
[51] Int. Cl.$^2$...................................... C07C 121/58
[58] Field of Search ............................... 260/465 G

[56] References Cited
UNITED STATES PATENTS
3,290,353  12/1966  Battershell et al................. 260/465

*Primary Examiner*—Lewis Gotts
*Assistant Examiner*—Dolph H. Torrence
*Attorney, Agent, or Firm*—Oblon, Fisher, Spivak, McClelland & Maier

[57] ABSTRACT

Tetrafluoroterephthalonitrile is produced by mixing tetrachloroterephthalonitrile, dry powdered potassium fluoride and a polar solvent having a water content of not more than 0.2% by weight and heating the resultant mixture with simultaneous agitation.

3 Claims, No Drawings

METHOD FOR MANUFACTURE OF TETRAFLUOROTEREPHTHALONITRILE

BACKGROUND OF THE INVENTION

This invention relates to a method for the manufacture of tetrafluoroterephthalonitrile by causing tetrachloroterephthalonitrile to react with dry powdered potassium fluoride having an excess fluorine content with reference to the chlorine content of tetrachloroterephthalonitrile in a polar solvent having a water content of not more than 0.2% by weight.

Having all the benzene rings to the exclusion of the nitrile group substituted with fluorine, tetrafluoroterephthalonitrile is useful in its unaltered form as a monomer or precussor for heat-resistant condensation polymers.

Among the methods for the manufacture of tetrafluoroterephthalonitrile, those which use fluorinated starting materials include a method which accomplishes the manufacture by amidating tetrafluoroterephthalic acid and subsequently dehydrating the resultant amide and a method which resorts to cyanation of 1,4-dibromotetrafluorobenzene (L. J. Belf et al, J. Chem. Soc., 1965, 3372).

Among the methods using nonfluorinated substances as the starting material, there is included, for example, a method which obtains tetrafluoroterephthalonitrile in a yield of 74% by allowing tetrachloroterephthalonitrile and potassium fluoride to react at 300°C for 5 hours in the absence of a solvent within an autoclave [K. Ueda et al, Bull. Chem. Soc. Japan, 40, 688 (1971)]. However, since this method causes the reaction to proceed at elevated temperatures in the absence of a solvent, it entails a disadvantage in terms of corrosiveness of the reaction vessel to be used. There is another method of this kind which obtains tetrafluoroterephthalonitrile in a yield of about 44% by causing the same raw materials to react in dimethylformamide at 130°to 145°C for 3 hours [Fr. Pat. No. 1,397,521 (1965)]. Although this method is advantageous in that the reaction is carried out at low temperatures, it involves formation of by-products and the yield of the desired product is low. Thus, this method is not commercially feasible.

An object of the present invention is to provide a method for manufacturing tetrafluoroterephthalonitrile easily in a high yield by fluorinating tetrachloroterephthalonitrile with potassium fluoride in a solvent.

SUMMARY OF THE INVENTION

To accomplish the object described above, the method according to the present invention causes tetrachloroterephthalonitrile and thoroughly dehydrated potassium fluoride to react with each other in a polar solvent having a water content of not more than 0.2% by weight at temperatures exceeding 130°C and not exceeding the boiling point of said solvent.

Since the overall water content of the reaction system is minimized because of the rigid control of water contents of the individual components, the otherwise possible occurrence of by-products is inhibited to the fullest extent and tetrafluoroterephthalonitrile, the product aimed at, is formed in a high yield. Furthermore, the reaction can be carried out easily because the reaction temperature is low. This reaction involves use of a solvent and, therefore, is free from the problem of corrosion of the reactor liable to ensue in the case of a solvent-less reaction.

The other objects and characteristic features of the present invention will be stated in the following detailed description of the invention.

DETAILED DESCRIPTION OF THE INVENTION

The inventors conducted researches into methods for the manufacture of tetrafluoroterephthalonitrile by low-temperature reaction of tetrachloroterephthalonitrile with potassium fluoride. They have consequently discovered that the water contained, though in a small proportion, in the starting materials or in the solvent is the cause for the low yield of said product obtained by any of the conventional methods. When water is present, though in a small proportion, in the reaction system, there occurs a water-soluble byproduct having a halogen group substituted with a hydroxyl group. Consequently, the yield of tetrafluoroterephthalonitrile is lowered to a great extent.

In view of the status of affairs described above, the inventors have now confirmed that tetrafluoroterephthalonitrile is obtained at low temperatures in a short period of time in a yield higher than that obtainable by the conventional method when tetrachloroterephthalonitrile is allowed to react in a polar solvent such as thoroughly dehydrated dimethylformamide with dry powdered potassium fluoride having an excess fluorine content with reference to the chlorine content of said tetrachloroterephthalonitrile at a temperature not exceeding the boiling point of said polar solvent.

The polar solvent to be used in the reaction is desired to have a water content of not more than 0.2% by weight. When this solvent has a higher water content than the upper limit mentioned above, it causes the halogen group adjoining the cyano group to be substituted with a hydroxyl group, with the result that a water-soluble by-product is formed and the yield of product is accordingly lowered.

Suitable polar solvents include dimethylformamide, diethylformamide, dimethylacetamide, N-methyl-2-pyrrolidone, dimethylsulfoxide, hexamethylphosphoramide and tetramethylenesulfone. Dimethylformamide, dimethylsulfoxide and N-methyl-2-pyrrolidone prove particularly desirable.

The amount in which potassium fluoride is added to tetrachloroterephthalonitrile is in the range of from 1.2 to 1.5 moles per atom of chlorine to be substituted. If it exceeds the upper limit 1.5 moles, the reaction velocity or the yield remains substantially the same. Conversely, the water content which can have an effect upon the reaction increases with the increasing amount of potassium fluoride added and, consequently, the yield is proportionally lowered. If the amount of potassium fluoride added is deficient, however, fluorination does not occur sufficiently and there ensues formation of a partial fluorination product. For the purpose of the reaction, potassium fluoride is heated, pulverized and then dried thoroughly before it is put to the reaction.

The potassium fluoride thus dried and pulverized and tetrachloroterephthalonitrile are added to a polar solvent and, while under vigorous agitation in a water-free atmosphere such as, for example, an atmosphere displaced with nitrogen gas or argon gas, are allowed to react with each other for 3 to 7 hours at temperatures exceeding 130°C and not exceeding the boiling point of the polar solvent. The reaction product is insolubilized itself in the mother liquid. So, it is separated by filtration or extracted with an organic solvent from the mother liquid, when washed with water and dried.

The reaction product obtained by the procedure just described invariably contains tetrafluoroterephthalonitrile of a purity exceeding 99% and the yield also rises above 50%.

As described above, the present invention produces tetrafluoroterephthalonitrile of high purity by a reaction which is carried out at low temperatures for a short period of time. And the reaction proceeds in a solvent. The method of this invention, therefore, can easily be practiced on a commercial scale without suffering from the problem of corrosion in the reactor.

The present invention will be described with reference to preferred embodiments. It is not limited by these examples.

EXAMPLE 1

Potassium fluoride was dired at 500°C and then pulverized. Dimethylformamide was desiccated over potassium hydroxide pellets and then distilled under nitrogen. The water content thereof was determined in dehydrated methanol by the Karl-Fischer method to be 0.02% by weight. A reactor having a reflux condenser, within which the atmosphere was displaced with nitrogen gas, was charged with 1.330 grams of tetrachloroterephthalonitrile, 1.743 grams of dry potassium fluoride and 10 milliliters of said dimethylformamide. Thereafter, the mixture was heated to 130°C with simultaneous agitation and allowed to undergo a reaction for five hours. Thereafter, the contents of the reactor were poured into ice water and a saturated aqueous solution of sodium chloride was added thereto. Consequently, the reaction product separated and floated to the surface. The floating phase was separated by filtration, washed with water and dried. The yield of the product was calculated to be 81.0%. Through analysis by the vapor-phase chromatography, the product was found to have a purity of 99.8%.

EXAMPLE 2:

Similarly to Example 1, a reactor was charged with 10 millimoles of tetrachloroterephthalonitrile, 60 millimoles of dried potassium fluoride and 10 milliliters of dimethylformamide (having a water content of 0.13%) and the resultant mixture was agitated at 130°C to induce a reaction. The relation between the composition of formed fluorinated products and the length of reaction time was as shown in Table 1.

Table 1

| Time (hour) | $F_4$ | p-$C_6F_nCl_{4-n}(CN)_2$ $F_3$ | $F_2$ | (by weight%) $F_1$ | $F_0$ |
|---|---|---|---|---|---|
| 0.5 | 1.9 | 32.6 | 62.9 | 2.6 | — |
| 1 | 22.7 | 55.3 | 22.0 | — | — |
| 2 | 64.6 | 32.6 | 2.8 | — | — |
| 3 | 88.6 | 11.4 | — | — | — |
| 5 | 94.4 | 5.6 | — | — | — |
| 7 | 95.4 | 4.6 | — | — | — |

As is clear from the foregoing table, tetrafluoroterephthalonitrile accounted for about 90% of the fluorinated products obtained at the end of 3 hours of reaction.

EXAMPLE 3

By following the procedure of Example 1, the same reaction was carried out, except that the amounts of tetrachloroterephthalonitrile and potassium fluoride, the kind of solvent, the water content, the reaction time and the reaction temperature were varied from one test run to another. The results were as shown in Table 2. The values of yield given in the table are those in terms of refined tetrafluoroterephthalonitrile.

Table 2

| p-$C_6Cl_4(CN)_2$ (mole) | KF (mole) | Solvent (ml) | $H_2O$ content (% by weight) | Reaction temperature (°C) | Reaction time (hr) | Yield (%) |
|---|---|---|---|---|---|---|
| 0.005 | 0.030 | DMF 10 | 0.13 | 130 | 3 | 62.4 |
| " | " | " " | " | 160 | " | 57.8 |
| " | 0.060 | " " | " | 130 | " | 48.0 |
| " | 0.030 | " " | 0.02 | 130 | 5 | 80.8 |
| " | " | NMP " | 0.08 | 160 | 3 | 53.5 |
| " | " | DMSO " | 0.13 | 130 | " | 50.9 |

DMF Dimethylformamide
NMP N-methyl-2-pyrrolidone
DMSO Dimethylsulfoxide

We claim:
1. A method for the manufacture of tetrafluoroterephthalonitrile, which comprises mixing tetrachloroterephthalonitrile, from 0.2 to 1.5 moles per atom of chloride of said tetrachloroterephthalonitrile of dry powdered potassium fluoride and a polar solvent selected from the group consisting of dimethylformamide, diethylformamide, dimethylacetamide, N-methyl-2-pyrrolidone, dimethylsulfoxide, hexamethylphosphoramide and tetramethylenesulfone having a water content of not more than 0.2% by weight, heating the resultant mixture at temperatures not exceeding the boiling point of said polar solvent but exceeding 130°C with simultaneous agitation and thereby causing formation of tetrafluoroterephthalonitrile in said mixture and separating from the mixture the formed tetrafluoroterephthalonitrile.

2. The method according to claim 1, wherein the polar solvent is dimethylformamide, dimethylsulfoxide or N-methyl-2-pyrrolidone and the water content of said polar solvent is not more than 0.05% by weight.

3. The method according to claim 1, wherein the separation of tetrafluoroterephthalonitrile is effected by salting out.

* * * * *